United States Patent [19]

Aslam et al.

[11] Patent Number: 5,087,769

[45] Date of Patent: Feb. 11, 1992

[54] PREPARATION OF 6-SUBSTITUTED-2-VINYLNAPHTHALENE

[75] Inventors: Mohammad Aslam, Corpus Christi, Tex.; Henry C. Linstid, III., Clinton, N.J.; Kenneth G. Davenport, North Kingstown, R.I.

[73] Assignee: Hoechst Celanese Corporation, Somerville, N.J.

[21] Appl. No.: 588,212

[22] Filed: Sep. 26, 1990

[51] Int. Cl.$^5$ .................... C07C 39/14; C07C 23/36; C07C 43/13

[52] U.S. Cl. .................... 568/736; 568/25; 568/631; 568/632; 568/654; 568/735; 570/182; 570/183; 570/190; 585/500; 585/654

[58] Field of Search ............... 568/585, 735, 650, 631, 568/654, 736, 632; 570/189, 188, 191, 193, 182, 183; 585/500, 654, 616

[56] References Cited

U.S. PATENT DOCUMENTS

| | | | |
|---|---|---|---|
| 2,468,759 | 5/1949 | Johnson | 260/669 |
| 3,234,286 | 2/1966 | Lawrence | 260/592 |
| 4,182,916 | 1/1980 | Baskeyfield et al. | 568/735 |
| 4,593,125 | 6/1986 | Davenport et al. | 568/319 |
| 4,675,449 | 6/1987 | Davenport | 568/319 |

*Primary Examiner*—Werren B. Lone
*Attorney, Agent, or Firm*—Shirley L. Church; DePaoli & O'Brien

[57] ABSTRACT

A method of forming 6-substituted-2-vinyl naphthalene from a 2-substituted naphthalene compound wherein the substituent in the 2-position is an ortho-para directing electron-donating group not reactive with hydrogen fluoride, comprises contacting the naphthalene compound and an acylating agent with substantially anhydrous hydrogen fluoride to acylate the naphthalene compound to a 6-substituted-2-acylnaphthalene compound, hydrogenating the 6-substituted-2-acylnaphthalene compound to convert the 2-acyl substituent to an alcohol substituent, dehydrating the product of hydrogenation in the presence of a free radical inhibitor to convert the alcohol substituent to an olefinic substituent, and isolating the formed 6-substituted-2-vinylnaphthalene subsequent to the dehydration.

12 Claims, No Drawings

PREPARATION OF 6-SUBSTITUTED-2-VINYLNAPHTHALENE

BACKGROUND OF THE INVENTION

The present invention is directed to a novel process for preparing 6-substituted-2-vinylnaphthalene. In particular, the invention is directed to preparing 6-substituted-2-vinylnaphthalene from 2-substituted naphthalene and 6-substituted-2-acylnaphthalene.

6-substituted-2-acylnaphthalenes have use as precursors for aromatic monomers used in the formation of polymers, pharmaceuticals, and other value-added chemicals. There is much discussion in both the patent and the technical literature relative to producing the 6-substituted-2-acylnaphthalenes. Typically, the 6-substituted naphthalenes are acylated in the presence of a Friedel-Crafts catalyst. Early improvements in this field were based on attempts to find useful solvents for the Friedel-Crafts reaction. An example is U.S. Pat. No. 3,234,286 which describes the replacement of the very toxic nitrobenzene solvent with 2-nitro propane. Typically, the literature contained general comments that the Friedel-Crafts type acylation of 2-substituted naphthalenes could be carried out in the presence of any Friedel-Crafts catalyst. Usually the general statement was substantiated by particular reference to experiments using, e.g., aluminum chloride or zinc chloride catalyst in nitrobenzene or chlorinated hydrocarbons, or boron trifluoride optimally in the presence of hydrogen fluoride. Most often, the literature did not identify the position of the acyl substitution on the 2-substituted naphthalene ring or did not provide such substitution in the 6-position with sufficient selectivity that a large scale manufacturing program could be developed using the disclosed technology.

Using the teachings of the prior art, commercialization of the process has been difficult. Aluminum chloride, zinc chloride, and similar salts used as Lewis acid catalysts in their anhydrous state absorb water rapidly, hydrolyzing, and thus becoming useless in the reaction. Nitrobenzene and the polyhalogenated hydrocarbons utilized as solvents are high boiling, toxic materials, and as such are undesirable solvents.

Nitrohydrocarbons, in the presence of the water invariably required during the usual work-up, give rise to inseparable emulsions. Also, the usual Friedel-Crafts catalysts, when admixed with nitrohydrocarbons, generate a substantial exothermic reaction which can be difficult to control. Conversions are low. When using metal halides in nitrohydrocarbons, isomeric mixtures are common, causing additional separation steps to be necessary.

U.S. Pat. No. 4,593,125 relates to an improved process for the acylation of naphthalene substituted in the 2-position by an electron-donating substituent. The inventors' purpose was to develop precursors for aromatic monomers for polyesters, pharmaceuticals, and other value-added chemicals by obtaining nearly exclusively 6-substituted-2-acylnaphthalenes in high conversions with high regioselectivity. In the process disclosed in this mentioned patent, the naphthalene compound to be acylated is brought in contact with substantially anhydrous hydrogen fluoride and the acylating agent for a time sufficient to cause substantially complete conversion of the naphthalene compound to a 6-substituted-2-acylnaphthalene.

6-substituted-2-vinylnaphthalene also has prospective use as a monomeric precursor in the formation of aromatic polymers, as well as having pharmaceutical applications and applications as a precursor for various chemicals. A proposed route to forming vinylnaphthalene from ethylnaphthalene is disclosed in U.S. Pat. No. 2,468,759. As disclosed therein, ethylnaphthalene is oxidized to a mixture of methyl naphthyl carbinol and methyl naphthyl ketone. The methyl naphthyl ketone is hydrogenated to methyl naphthyl carbinol and the methyl naphthyl carbinol dehydrated to vinylnaphthalene. There is no disclosure of forming a 6-substituted-2-vinylnaphthalene in this patent. Moreover, it is not merely a simple procedure to hydrogenate the naphthone to the corresponding carbinol over broad conditions and any hydrogenation catalyst as overhydrogenation to the ethylnaphthalene readily results. In addition, the dehydration reaction must be controlled by use of process conditions and type of catalyst to prevent or to minimize the polymerization of the formed vinylnaphthalene.

Accordingly, it is an object of the present invention to provide an improved process for the production of 6-substituted-2-vinylnaphthalene.

SUMMARY OF THE INVENTION

The process of this invention begins with the regioselective acylation of naphthalene substituted in the 2-position by an electron-donating substituent. In this step of the invention, the naphthalenic compound to be acylated is brought in contact with substantially anhydrous hydrogen fluoride, contacted with an appropriate quantity of the acylating agent, and heated to from about 40° C. to about 100° C. for a time sufficient to cause substantially complete conversion of the naphthalene compound to a 6-substituted-2-acylnaphthalene. The hydrogen fluoride is then removed by evaporation and the naphthone is isolated. Although the initial step of the process of this invention is useful in acylating any appropriately substituted naphthalene, it is particularly useful in the acylation of compounds of the formula:

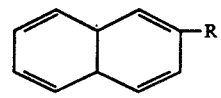

wherein R is hydroxy, lower alkyl, lower alkoxy, phenoxy, lower alkylthio, and halo.

The acylating agent useful in the process of the present invention may conveniently be any commercially useful acylating agent. The reaction is more particularly useful when carried out with the lower alkyl carboxylic acids, acid anhydrides, and acid halides.

In accordance with the process of this invention, the 6-substituted-2-acylnaphthalene is subsequently converted to 6-substituted-2-vinylnaphthalene by subjecting the naphthone to consecutive steps of hydrogenation to convert the carbonyl group to a hydroxy moiety and dehydration to dehydrate the alcoholic substituent to an olefinic substituent off the naphthalene ring. Thus, in this portion of the process, the 6-substituted-2-acylnaphthalene is contacted with hydrogen, preferably in the presence of a hydrogenation catalyst, to convert the carbonyl group to a substituent comprising the corresponding alcohol. Subsequent to the hydrogenation reaction, the 1-(6'-substituted-2'-naphthyl)alkanol is dehydrated in the presence of a dehydration catalyst to yield the olefinic substituent. During the dehydration step, a free radical inhibitor is used to prevent polymerization of the 6-substituted-2-vinylnaphthalene as it is formed. The substituent at the 6-position remains substantially unreacted.

DETAILED DESCRIPTION OF THE INVENTION

The invention can best be described by schematically illustrating the reaction steps which are proposed for converting a 2-substituted naphthalene to 6-substituted-2-vinylnaphthalene.

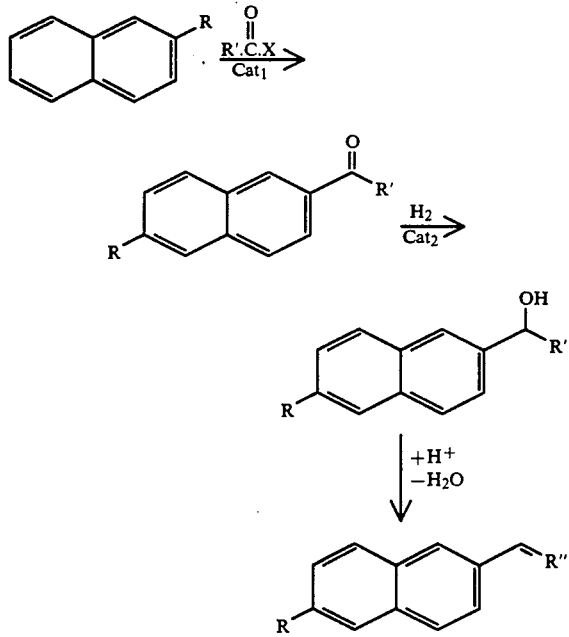

wherein R is a member of the group consisting of hydroxy, lower alkyl, lower alkoxy, phenoxy, and lower alkylthio and halo; X is selected from the group consisting of Fl, Cl, Br, OH, and

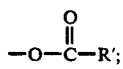

R' is a low molecular weight alkyl comprising from 1 to 4 carbon atoms; R'' is R' minus one H, e.g. R' is $CH_3$ and R'' is $CH_2$, R' is $CH_3-CH_2$ and R'' is $CH_3-CH$, R' is $CH_3-CH_2-CH_2$ and R'' is $CH_3-CH_2-CH$; $Cat_1$ is Friedel-Crafts catalyst, $Cat_2$ is one of the commonly known hydrogenation catalysts, such as Pd on carbon, Raney nickel, etc.

As dipicted above, the 6-substituted-2-acylnaphthalene can be prepared by acylating 2-substituted naphthalene. Typically, the starting compounds most useful in this initial stage of the process of the invention are characterized by the formula:

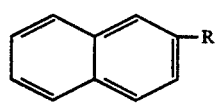

wherein R is a member of the group consisting of hydroxy, lower alkyl, lower alkoxy, phenoxy, lower alkylthio, and halo.

As used in the context of this invention: Lower alkyl means $C_1$ to $C_4$ alkyl and includes the methyl, ethyl, n-propyl, iso-propyl, n-butyl, sec-butyl, iso-butyl, and tert-butyl moieties.

Lower alkoxy is meant to be a member of the group consisting of methoxy, ethoxy, n-propoxy, iso-propoxy, n-butoxy, sec-butoxy, iso-butoxy, and tert-butoxy.

Lower alkylthio is methylthio, ethylthio, n-propylthio, iso-propylthio, n-butylthio, sec-butylthio, isobutylthio or tert-butylthio.

Halo includes fluoro, chloro, bromo, and iodo.

Compounds particularly useful in the process of this invention include: 2-naphthol, 2-methylnaphthalene, 2-ethylnaphthalene, 2-isopropylnaphthalene, 2-methoxynaphthalene, 2-ethoxynaphthalene, 2-methylthionaphthalene, 2-ethylthionaphthalene, 2-fluoronaphthalene, 2-chloronaphthalene,2-bromonaphthalene, and the like.

The acylating agent most particularly useful for the present invention process includes a lower alkyl carboxylic acid or a derivative of a lower alkyl carboxylic acid, as for example, a carboxylic acid halide or anhydride, wherein by lower alkyl is meant the $C_2-C_4$ carboxylic acids and derivatives thereof.

Examples of acylating agents particularly useful in the present invention include acetic acid, propionic acid, butyric acid, isobutyric acid, acetic anhydride, propionic anhydride, acetyl chloride, propionyl chloride, acetyl fluoride, propionyl fluoride, butyryl fluoride, acetyl bromide, propionyl bromide, and the like.

The acylating step can be operated in a batch or semi-continuous manner. The acylating step of the process should be run in a closed system since hydrogen fluoride is a toxic material which has a high vapor pressure, boiling at about ambient room temperature, and the acylation step is carried out normally at above ambient room temperature, as for example, at about 60° C. to about 80° C.

The acylation step of the process is normally carried out in the following manner. The appropriately substituted naphthalene is brought into contact with substantially anhydrous hydrogen fluoride. Although an excess of hydrogen fluoride is acceptable and does not cause an appreciable loss of yield or regioselectivity, it is most advantageous to use about a 1:25 to about 1:50 mole ratio of naphthalene derivative to hydrogen fluoride.

The reaction can be carried out in the absence of an additional solvent. However, it is not detrimental to the reaction to use an additional inert solvent. Typically, such additional solvents may include a chlorinated hydrocarbon or the like.

The mixture is cooled to at least about −30° C. preferentially by contacting the vessel containing the mixture with a cryogenic mixture of liquefied gases, solid carbon dioxide or a similar material. The acylating agent is added and the reaction vessel sealed in a manner to withstand the vapor pressure of the hydrogen fluoride at the reaction temperature. The cooling of the reaction vessel prior to addition of the acylating agent is only for the purpose of minimizing any reaction which might occur in admixing.

Typically, then, the reaction vessel is heated to the temperature of reaction. In the process herein described, although some reaction does occur at temperatures below about 40° C., as for example, at ambient room temperature, the greatest conversion to and the greatest regioselectivity to the 2-acyl-6-substituted naphthalene occurs between about 40° C. and about 100° C. In a preferred embodiment, the reaction occurs at a temperature range of from about 60° C. to about 80° C.

In a preferred embodiment, a reaction time at the preferred temperature range of about 60 minutes gives rise to a high conversion of starting material to a product of which the acyl isomers contain a high proportion of the desired product without the formation of substantial quantities of undesired by-products.

The order of addition of the individual reactants and hydrogen fluoride, as described above, is only explicative. It is also to be considered to be within the scope of the invention to mix the 2-substituted naphthalene and the acylating agent, cool to below the boiling point of hydrogen fluoride, and to then add the hydrogen fluoride and any inert solvent; adding the 2-substituted naphthalene to a cooled solution of the acylating agent in hydrogen fluoride is also to be considered to be an equivalent method to carry out the adding or mixing step of the process of this invention. The acylation step is described in detail in U.S. Pat. No. 4,593,125 herein incorporated by reference.

The next step of the process of this invention involves the conversion of the 6-substituted-2-acylnaphthalene to 6-substituted-2-vinylnaphthalene. This stage of the process will be described with respect to converting 6-substituted-2-acylnaphthalene to 6-substituted-2-vinylnaphthalene for the sake of understanding the invention. It is to be understood, however, that the invention pertains to 2-substituted naphthalenes which have been acylated with acylating agents containing 2 to 4 carbon atoms. Thus, this step of the process comprises the sequential hydrogenation and dehydration of the acylated product as shown schematically above.

For example, in this stage of the process, 6-substituted-2-acylnaphthalene is hydrogenated to 1-(6'-substituted-2'-naphthyl)ethanol. Hydrogenation takes place at a hydrogen pressure of from between about 50 to 500 psig, and at a temperature from between about 50° to 175° C. A hydrogenation catalyst is present in the reaction medium. Any hydrogenation catalyst can be utilized. For example, the group VIII metals including nickel, palladium, platinum, ruthenium, etc. can be used. Copper chromite is also useful in hydrogenating 6-substituted-2-acylnaphthalene. The catalyst can be used unsupported or it can be supported on a suitable carrier such as silica, alumina, silica-alumina, and like carriers. Carbon is also a suitable carrier for the hydrogenation catalyst.

Subsequent to hydrogenation, the hydrogenated product may be treated to recover the desired 1-(6'-substituted-2'-naphthyl)ethanol in a relatively pure form. This may be effected by distilling the crude hydrogenation product at a pressure sufficiently below atmospheric to give a temperature below that which substantial dehydration of the carbinol substituent takes place.

In accordance with the invention, the 1-(6'-substituted-2'-naphthyl)ethanol produced from the hydrogenation step is converted to 6-substituted-2-vinylnaphthalene by passing the 1-(6'-substituted-2'-naphthyl)ethanol in contact with a dehydration catalyst which suitably is a surface catalyst such as activated alumina. Under suitable conditions of temperature and pressure, dehydration of the carbinol substituent is effected. At a temperature of at least 130° C. at about 1 to about 10 mm Hg, and in the pressure of a suitable dehydration catalyst, 1-(6'-substituted-2'-naphthyl)ethanol may be substantially completely dehydrated. A free radical inhibitor is used to prevent polymerization of the 6-substituted-2-vinylnaphthalene as it is formed. The concentration of free radical inhibitor typically ranges between about 100 ppm and about 1% by weight based on the amount of alcohol fed to the reaction. Any of the commonly known free radical inhibitors, such as, for example, t-butyl catechol, hydroquinone, and phenothiazine can be used, with increased concentration typically being dependent on the kind of substituent group on the naphthalene ring.

As an additional precaution to avoid polymerization of the ensuing vinylnaphthalene during the dehydration, it is necessary to effect a suitable balance between the temperature of the dehydration reaction and the time of exposure. If the temperature is too high or if the time is too low, undesirable polymerization of vinylnaphthalene takes place. It has been found that using the free radical inhibitors described above and dehydration temperatures between about 130° C. and 200° C., with a surface catalyst, such as KHSO$_4$, p-toluenesulfonic acid, methanesulfonic acid, phosphoric acid, ammonium bisulfite, etc., the space-velocity may easily be so regulated as to obtain high conversion of the secondary alcohol to a vinyl group attached to the naphthalene ring with substantially no polymerization.

The dehydration is most suitably effected at atmospheric pressure although higher or lower pressures, while not economical, nevertheless may be used. It is desirable to reduce the partial pressure of the 1-(6'-substituted-2'-naphthyl)ethanol vapors over the surface catalyst by diluting them with a suitable inert diluent gas such as carbon dioxide.

A product may be thus obtained which is sufficiently pure for technical purposes. Where a more highly refined product is desired, however, or where the dehydration through inactivation of catalyst leaves a substantial proportion of the carbinol substituent unchanged, the product may be purified by distillation at a pressure sufficiently below atmospheric to give a temperature below that at which substantial polymerization of vinylnaphthalene takes place.

The process according to this invention including reaction and recovery of the product is illustrated in greater detail in the following examples. Unless otherwise indicated, all percentage amounts are weight percent.

EXAMPLE

Step 1: Preparation of 6-methoxy-2-acetonaphthone

A 2.0 gallon Hastelloy C autoclave was charged with 2-methoxynaphthalene (420 g, 2.66 mol) and acetic anhydride (298 g, 2.9 mol). The reactor was closed, cooled (−40° C.) and evacuated with a water aspirator. Anhydrous HF (2.1 kg, 106 mol) was transferred to the reactor. The reactor was warmed up to room temperature and then heated at 80° C. for 2 hours. After the heating period was over, the reactor was cooled to room temperature and HF was vented to a KOH scrubber. After all the HF was vented, the contents of the reactor were diluted with ethyl acetate (5 L) and poured on crushed ice. The pH of the reaction mixture was adjusted to 7.0 with 45% aqueous KOH. The ethyl acetate layer was separated, washed with water, dried over anhydrous magnesium sulfate and concentrated to give crude 6-methoxy-2-acetonaphthone (497 g). The crude product was distilled (0.1 mm) to afford a solid (398 g). The solid was recrystallized with glacial acetic acid and water to afford pure 6-methoxy-2-acetonaphthone (376 g).

Step 2: Preparation of 1-(6′methoxy-2′-naphthyl)ethanol

A 500 c.c. stainless steel reactor was charged with 6-methoxy-2-acetonaphthone (60 g, 0.3 mol), methanol (200 mL) and 5% Pd/C (51% wet) (4.8 g). The reactor was heated to 50° C. and stirred for 3 hours. The reactor was vented, catalyst removed via filtration and the solvent removed on the rotary-evaporator to afford a solid. Recrystallization with acetic acid/water afforded 96% pure 1-(6′methoxy-2′naphthyl)ethanol (57 g).

Step 3: Preparation of 6-methoxy-2-vinylnaphthalene 1-(6′-methoxy-2′-naphthyl)ethanol (20.2 g, 0.1 mol), potassium bisulfate (0.15 g) and t-butyl catechol (0.15 g) was charged to a round bottom flask. The flask was attached to Kugel-Rohr apparatus and a vacuum pump, and heated gradually. When the outside temperature reached 130° C., the vacuum was turned on. Most of the product distilled at 130°–180° C. The product was recrystallized with absolute alcohol to afford 100% pure 6-methoxy-2-vinylnaphthalene (6.7 g).

What is claimed is:

1. A method of forming 6-substituted-2-vinyl-naphthalene from a 2-substituted naphthalene compound of the formula:

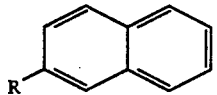

wherein R is an ortho-para directing electron-donating group not reactive with hydrogen fluoride, comprising:
 a) contacting a reaction mixture of said 2-substituted naphthalene compound and an acylating agent with substantially anhydrous hydrogen fluoride at a temperature ranging from about 40° C. to about 100° C. for a time sufficient to cause substantially complete acylation of the naphthalene compound to a 6-substituted-2-acylnaphthalene compound;
 b) hydrogenating said 6-substituted-2-acylnaphthalene compound at a hydrogen pressure ranging from about 50 to about 500 psig, and at a temperature ranging from about 50° C. to about 175° C. for a time period sufficient to convert the carbonyl substituent to a hydroxy moiety; and
 c) dehydrating the product of said hydrogenation in the presence of a free radical inhibitor under vacuum, at a temperature of at least 130° C. to convert said hydroxy moiety to an olefinic substituent, and isolating the formed 6-substituted-2-vinylnaphthalene subsequent to the dehydration.

2. The method of claim 1 wherein the acylating agent is a member of the group consisting of lower alkyl carboxylic acids, lower alkyl carboxylic acid anhydrides, and lower alkyl carboxylic acid halides.

3. The method of claim 1 wherein R is a member of the group consisting of hydroxy, lower alkyl, lower alkoxy, lower alkylthio and halo.

4. The method of claim 1 wherein the temperature of acylation is from about 60° to about 80° C. and the time of reaction is from about 30 to about 180 minutes.

5. The method of claim 1 wherein the naphthalene compound to hydrogen fluoride mole ratio in the reaction mixture is from about 1:25 to about 1:50.

6. The method of claim 2 wherein said acetylating agent is acetic anhydride.

7. The method of claim 1 wherein said hydrogenation takes place in the presence of a hydrogenation catalyst.

8. The method of claim 1 wherein said dehydration takes place in the presence of a dehydration catalyst.

9. A method of forming 6-substituted-2-vinylnaphthalene from a 6-substituted-2-acylnaphthalene compound of the formula:

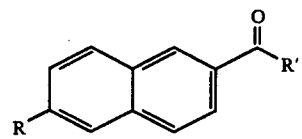

wherein R is an ortho-para directing electron-donating group not reactive with hydrogen fluoride, and R′ is an alkyl group containing 1 to 4 carbon atoms, comprising:
 a) hydrogenating said 6-substituted-2-acylnaphthalene compound at a hydrogen pressure ranging from about 50 to 500 psig, and at a temperature ranging from about 50° C. to about 175° C. for a time period sufficient to convert the carbonyl substituent to a hydroxy moiety; and
 b) dehydrating the product of said hydrogenation in the presence of a free radical inhibitor under vacuum, at a temperature of at least 130° C. to convert said hydroxy moiety to an olefinic substituent.

10. The method of claim 9 wherein said hydrogenation takes place in the presence of a hydrogenation catalyst.

11. The method of claim 9 wherein said dehydration takes place in the presence of a dehydration catalyst.

12. The method of claim 9 wherein R is a member of the group consisting of hydroxy, lower alkyl, lower alkoxy, thio, lower alkylthio and halo.

* * * * *

UNITED STATES PATENT AND TRADEMARK OFFICE
CERTIFICATE OF CORRECTION

PATENT NO. : 5,087,769

DATED : February 11, 1992

INVENTOR(S) : Aslam, et al

It is certified that error appears in the above-identified patent and that said Letters Patent is hereby corrected as shown below:

Column 5, line 68, "pressure" should read --presence--.

Signed and Sealed this

Twentieth Day of April, 1993

*Attest:*

MICHAEL K. KIRK

*Attesting Officer*     *Acting Commissioner of Patents and Trademarks*